United States Patent [19]

Boehner et al.

[11] 4,044,124
[45] * Aug. 23, 1977

[54] TRIAZOLYLPHOSPHORUS COMPOUNDS

[75] Inventors: Beat Boehner, Binningen; Dag Dawes, Pratteln; Willy Meyer, Basel, all of Switzerland

[73] Assignee: Ciba-Geigy Corporation, Ardsley, N.Y.

[*] Notice: The portion of the term of this patent subsequent to Feb. 18, 1992, has been disclaimed.

[21] Appl. No.: 614,733

[22] Filed: Sept. 18, 1975

Related U.S. Application Data

[63] Continuation-in-part of Ser. No. 572,785, April 29, 1975, abandoned, which is a continuation of Ser. No. 310,726, Nov. 30, 1972, abandoned.

[30] Foreign Application Priority Data

Dec. 10, 1971 Switzerland .......................... 18064/71
Sept. 29, 1972 Switzerland .......................... 14252/72

[51] Int. Cl.$^2$ ..................... C07D 249/12; A01N 9/36
[52] U.S. Cl. .................. 424/200; 260/308 R; 260/308 C
[58] Field of Search .................... 260/308 R; 424/200

[56] References Cited

U.S. PATENT DOCUMENTS 3,232,830  2/1966  Schrader et al. ................ 260/308 R
3,862,124  1/1975  Dawes et al. .................... 260/308 R
3,867,398  2/1975  Bohner et al. ................... 260/308 R

FOREIGN PATENT DOCUMENTS 2,057,170  5/1971  Germany

OTHER PUBLICATIONS

Scherer et al, C.A. 71, 101861c (1969).

Primary Examiner—Raymond V. Rush
Attorney, Agent, or Firm—Harry Falber

[57] ABSTRACT

Triazolylphosphorus compounds of the formula

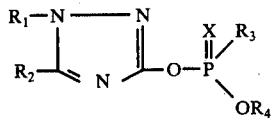

(I)

wherein
  $R_1$ represents $C_1-C_5$-alkyl, cyclopentyl, cyclohexyl or unsubstituted phenyl,
  $R_2$ represents $C_1-C_5$-alkoxy or phenoxy,
  $R_3$ represents $C_1-C_5$-alkyl, $C_1-C_5$-alkoxy or $C_1-C_5$-alkylthio,
  $R_4$ represents $C_1-C_5$-alkyl, and
  X represents oxygen or sulfur, and their use in pest control.

6 Claims, No Drawings

TRIAZOLYLPHOSPHORUS COMPOUNDS

RELATED APPLICATION

This is a continuation-in-part of application Ser. No. 572,785 filed Apr. 29, 1975, now abandoned, which in turn, is a continuation of application Ser. No. 310,726, filed Nov. 30, 1972, now abandoned. The present invention relates to triazolylphosphorus compounds and their use in pest control. These triazolylphosphorus derivatives correspond to the formula

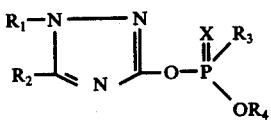

(I)

wherein
$R_1$ represents $C_1$-$C_5$-alkyl, cyclopentyl, cyclohexyl or unsubstituted phenyl,
$R_2$ represents $C_1$-$C_5$-alkoxy or phenoxy,
$R_3$ represents $C_1$-$C_5$-alkyl, $C_1$-$C_5$-alkoxy or $C_1$-$C_5$-alkylthio,
$R_4$ represents $C_1$-$C_5$-alkyl and
X represents oxygen or sulfur.

The alkyl, alkoxy and alkylthio groups, suitable for $R_1$ to $R_4$ may be branched or straight-chain. Examples of such groups are: methyl, methoxy, methylthio, ethyl, ethoxy, ethylthio, propyl, propoxy, propylthio, isopropyl, isopropoxy, isopropylthio, n-butyl, n-butoxy, n-butylthio, i-butyl, sec.-butyl, tert.-butyl, n-pentyl, n-pentoxy, n-pentylthio and isomers thereof.

Preferred compounds of formula I because of their effectiveness are compounds of the formula

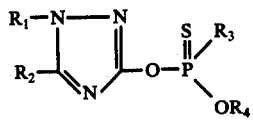

(Ia)

wherein
$R_1$ represents $C_1$-$C_5$-alkyl,
$R_2$ represents $C_1$-$C_5$-alkoxy,
$R_3$ represents $C_1$-$C_5$-alkyl, $C_1$-$C_5$-alkoxy or $C_1$-$C_5$-alkylthio and
$R_4$ represents $C_1$-$C_5$-alkyl.

The compounds of formula I are produced by the reaction of a. a hydroxy-triazole of the formula

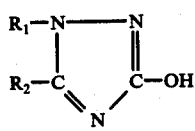

(II)

wherein $R_1$ and $R_2$ have the meanings given under formula I with a phosphoric acid halide of the formula

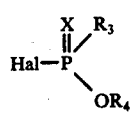

(III),

Wherein Hal represents a chlorine or broimine, X, $R_3$ and $R_4$ have the meanings given under formula I, in the presence of an acid-binding agent, or by the reaction of b. a metal salt of a hydroxy-triazole of formula II with a phosphoric acid halide of formula III.

Suitable salts of hydroxy-triazoles of formula II for the process according to the invention are, in particular, the alkali metal salts; there are however others which are suitable, e.g. salts of monavalent heavy metals.

Suitable acid-binding agents are, for example, the following bases: tertiary amines such as triethylamine, dimethylaniline, pyridine, inorganic bases such as hydroxides and carbonates of alkali and alkaline-earth metals, preferably sodium and potassium carbonate.

The reactions are preferably carried out in so vents or diluents which are inert to the reactants. The following, for example, are suitable: aromatic hydrocarbons such as benzene, toluene, ligroins, halogenated hydrocarbons, chlorobenzene, polychlorobenzenes, bromobenzene, chlorinated alkanes having 1 to 3 carbon atoms, ethers such as dioxane, tetrahydrofuran; esters such as ethyl acetate; ketones such as methyl ethyl ketone, diethyl ketone, nitriles, e.g. acetonitrile.

The starting materials of formula II are in some cases known, or can be produced by reaction of an imino compound of the formula

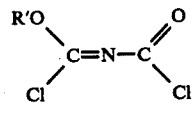 or

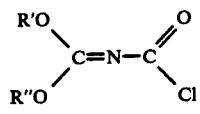 or

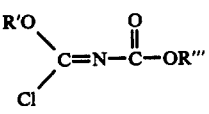 or

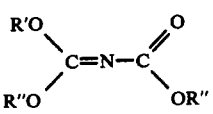

with a hydrazine of the formula

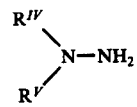

whereby in the formulae the symbols R', R" and R''' represent $C_1$-$C_5$-alkyl or unsubstituted phenyl, $R^{IV}$ represents hydrogen or $C_1$-$C_5$-alkyl, and $R^V$ represents hydrogen $C_1$-$C_5$-alkyl or unsubstituted phenyl.

Furthermore, products of formula II can be obtained from 5-halogen-3-hydroxy 1,2,4-triazoles by reaction with alcoholates or phenolate.

The compounds of formula I have a broad biocidal action, and can be used for the control of diverse plant and animal pests. The said compounds are suitable, in particular, for the control of insects of the families: *Acrididae, Blattidae, Gryllotalpidae, Tettigoniidae Cimicidae, Pyrrhocoridae, Reduviidae, Aphididae, Delphacidae, Diaspipidiade, Pseudococcidae, Chrysomelidae, Coccinelliadae, Bruchidae, Scarabaeidae, Dermestidae, Teneb-* rionidae, Curculionidae, Tineidae, Noctuidae, Lymantriidae, Pyralidae, Galleriidae, Culicidae, Tipulidae, Stomoxydae, Muscidae, Calliphoridae, Trypetidae, Pulicidae, as well as acarids of the families: *Ixodidae, Argasidae, Tetranychidae, Dermanyssidae.*

The insecticidal and/or acaricidal action can be substantially broadened and adapted to suit the particular circumstances by the addition of other insecticides and/or acaricides. Suitable additives include, for example, organic phosphorus compounds, nitrophenols and derivatives, pyrethorus and analogeous compounds, formamidines, ureas, carbamates and chlorinated hydrocarbons. The agents according to the invention are prepared in a known manner by the initimate mixing and/or grinding of the active substance of formula I with suitable carriers, optionally with the addition of dispersing agents or solvents which are inert to the active substances. The active substances can be obtained and used in the following form:

| solid preparations: | dusts, scattering agents, granulates, coated granulates, impregnated granulates and homogeneous granulates; |
|---|---|
| liquid preparations: | a) water-dispersible active substance concentrates; wettable powders, paste, or emulsions<br>b) solutions. |

The content of active substance in the described agents is between 0.1 and 0.5%; it is to be mentioned in this connection that in the case of application from an aeroplane, or by means of other suitable devices, concentrations of up to 99.5% can be employed, or even the pure active substance.

The active substance of formula I can be prepared, for example, as follows:

DUSTS:

The following substances are used in the preparation of a. a 5% dust and b. a 2% dust:

a. 5 parts of active substance, 95 parts of talcum;

b. 2 parts of active substance, 1 part of highly dispersed silicic acid 97 parts of talcum.

The active substances are mixed and ground with the carriers.

GRANULATE:

The following substances are used to produce a 5% granulate:

5 parts of active substance,
0.25 parts of epichlorhydrin,
0.25 parts of cetyl polyglycol ether,
3.50 parts of polyethylene glycol,
91 parts of kaolin (particle size 0.3–0.8 mm).

The active subtance is mixed with epichlorhydrin and dissolved with 6 parts of acetone; the polyethylene glycol and cetyl polyglycol ether are then added. The solution thus obtained is sprayed on to kaolin, and the acetone subsequently evaporated off in vacuo.

WETTABLE POWDER:

The following constituents are used for the preparation of a. a 40%, b. and c. a 25%, and d. a 10% wettable powder:

| | | |
|---|---|---|
| a) | 40 | parts of active substance, |

-continued

| | | |
|---|---|---|
| | 5 | parts of sodium lignin sulphonate, |
| | 1 | part of sodium dibutyl-naphthalene sulphonate, |
| | 54 | parts of silicic acid. |
| b) | 25 | parts of acitve substance, |
| | 4.5 | parts of calcium lignin sulphonate, |
| | 1.9 | parts of Champagne chalk/hydroxyethyl cellulose mixture (1:1), |
| | 1.5 | parts of sodium dibutyl naphthalene sulphonate, |
| | 19.5 | parts of silicic acid, |
| | 19.5 | parts of Champagne chalk, |
| | 28.1 | parts of kaolin. |
| c) | 25 | parts of active substance, |
| | 2.5 | parts of isooctylphenoxy-polyoxyethylene-ethanol, |
| | 1.7 | parts of Champagne chalk/hydroxyethyl cellulose mixture (1:1), |
| | 8.3 | parts of sodium aluminum silicate, |
| | 16.5 | parts of kieselguhr, |
| | 46 | parts of kaolin. |
| d) | 10 | parts of active substance, |
| | 3 | parts of a mixture of the sodium salts of saturated fatty alcohol sulphates, |
| | 5 | parts of naphthalenesulphonic acid/formaldehyde condensate, |
| | 82 | parts of kaolin. |

The active substance is intimately mixed, in suitable mixers, with the additives, and the mixture then ground in the appropriate mills and rollers. Wettable powders are obtained which can be diluted with water to give suspensions of any desired concentration.

EMULSIFIABLE CONCENTRATES:

The following substances are used to produce a. a 10% and b. a 25% emulsifiable concentrate:

| | | |
|---|---|---|
| a) | 10 | parts of active substance, |
| | 3.4 | parts of epoxidised vegetable oil, |
| | 3.4 | parts of a combination emulsifier consisting of fatty alcohol polyglycol ether and alkylaryl-sulphonate calcium salt, |
| | 40 | parts of dimethylformamide, |
| | 43.2 | parts of xylene. |
| b) | 25 | parts of active substance, |
| | 2.5 | parts of epoxidised vegetable oil, |
| | 10 | parts of an alkylarylsulphonate/fatty alcohol-polyglycol ether mixture, |
| | 5 | parts of dimethylformamide, |
| | 57.5 | parts of xylene. |

From these concentrates it is possible to produce, by dilution with water, emulsions of any desired concentration.

SPRAY:

The following constituents are used to prepare a 5% or a 95% spray 5 parts of active substance,
1 part of epichlorhydrin,
94 parts of ligroin (boiling limits 160° –190° C). or
95 parts of active substance,
5 of epichlorhydrin.

EXAMPLE 1

Production of the starting material:

1-Isopropyl-3-hydroxy-5-methoxy-1,2,4-triazole

An amount of 166 g of 1-isopropyl-3-hydroxy-5-chloro-1,2,4-triazole is added to a solution of 115 g of sodium in 1000 ml of methanol; the mixture is then refluxed for 15 hours. After separation of filtration of the precipitated sodium chloride, and concentration of the filtrate in vacuo, the residue is taken up in dilute acetic acid and extracted twice with ether. The ether is evaporated off, and the partially crystalline residue dissolved in a little methanol. On cooling of the solution to −70° C, the product crystallises out. There is thus obtained 43.5 g of 1-isopropyl-3-hydroxy-5-methoxy-1,2,4-triazole in the form of white crystals, M.P. 102°–103° C.

PRODUCTION OF THE NEW PHOSPHOROUS COMPOUNDS a. 0,0-diethyl-0-[1-isopropyl-5-methoxy-1,2,4-triazolyl-(3)]-thiophosphate

A mixture of 15.2 g of 1-isopropyl-3-hydroxy-5-methoxy-1,2,4-triazole and 13.8 g of potassium carbonate in 500 ml. of methyl ethyl ketone is refluxed for one hour. An addition is then made at 50° C. of 19.0 g of 0,0-diethylthiophosphoric acid chloride, and the mixture refluxed for 1½ hours. After the precipitated salts have been filtered off through Hyflo, the filtrate is concentrated in vacuo to obtain the compound of the formula in the form of pale yellow oil, $n_D^{20} = 1.4773$.

b. 0-Ethyl-S-n-propyl-0-[1-isopropyl-5-methoxy-1,2,4-triazolyl-(3)]-dithiophosphate A mixture of 15.3 g of 1-isopropyl-3-hydroxy-5-methoxy-1,2,4-triazole, 13.8 g of potassium carbonate and 500 ml. of acetonitrile is refluxed for two hours, and then cooled at room temperature; and addition is subsequently made of 22.0 g of O-ethyl-S-n-propyl-dithiophosphoric acid chloride, and the whole thereupon refluxed for two hours. There is obtained, after processing, the compound of the formula as yellow oil, $n_D^{20} = 1.5120$.

The following compounds too are produced analogously:

$n_D^{20} = 1.4880$ $n_D^{20} = 1.4783$ $n_D^{20} = 1.4893$

The following compounds too could be obtained in an analogous manner

| $R_1$ | $R_2$ | $R_3$ | $R_4$ | X |
|---|---|---|---|---|
| $-C_3H_{7(i)}$ | $-OCH_3$ | $-OCH_3$ | $-CH_3$ | S |
| $-C_3H_{7(i)}$ | $-OCH_3$ | $-OC_2H_5$ | $-C_2H_5$ | O |
| $-C_3H_{7(i)}$ | $-OCH_3$ | $-C_2H_5$ | $-C_2H_5$ | S |
| $-C_3H_{7(i)}$ | $-OCH_3$ | $-CH_3$ | $-C_2H_5$ | S |
| $-C_3H_{7(i)}$ | $-OCH_3$ | $-CH_3$ | $-C_3H_{7(n)}$ | S |
| $-C_3H_{7(i)}$ | $-OCH_3$ | $-SC_3H_{7(n)}$ | $-C_2H_5$ | S |
| $-C_3H_{7(i)}$ | $-OC_2H_5$ | $-OC_2H_5$ | $-C_2H_5$ | S |
| $-C_3H_{7(i)}$ | $-OC_2H_5$ | $-OCH_3$ | $-CH_3$ | S |
| $-C_3H_{7(i)}$ | $-OC_2H_5$ | $-SC_3H_{7(n)}$ | $-C_2H_5$ | S |
| $-C_3H_{7(i)}$ | $-OC_2H_5$ | $-C_2H_5$ | $-C_2H_5$ | S |
| $-C_3H_{7(i)}$ | $-OC_3H_{7(n)}$ | $-OC_2H_5$ | $-C_2H_5$ | S |
| $-C_3H_{7(i)}$ | $-OC_4H_{9(n)}$ | $-OC_2H_5$ | $-C_2H_5$ | S |
| $-C_3H_{7(i)}$ | $-O-\langle\text{Ph}\rangle$ | $-OC_2H_5$ | $-C_2H_5$ | S |
| $-C_3H_{7(i)}$ | $-O-\langle\text{Ph}\rangle$ | $-OCH_3$ | $-CH_3$ | S |
| $-C_3H_{7(i)}$ | $-O-\langle\text{Ph}\rangle$ | $-SC_3H_{7(n)}$ | $-C_2H_5$ | S |
| $-CH_3$ | $-OC_3H_{7(i)}$ | $-OC_2H_5$ | $-C_2H_5$ | S |
| $-CH_3$ | $-OC_3H_{7(i)}$ | $-SC_3H_{7(n)}$ | $-C_2H_5$ | S |
| $-CH_3$ | $-OC_3H_{7(i)}$ | $-C_2H_5$ | $-C_2H_5$ | S |
| $-CH_3$ | $-O-CH_3$ | $-OC_2H_5$ | $-C_2H_5$ | S |
| $-\langle\text{Ph}\rangle$ | $-OCH_3$ | $-OC_2H_5$ | $-C_2H_5$ | S |
| $-\langle\text{Ph}\rangle$ | $-OC_2H_5$ | $-OC_2H_5$ | $-C_2H_5$ | S |
| $-CH_3$ | $-OC_2H_5$ | $-OC_2H_5$ | $-C_2H_5$ | S |
| $-CH_3$ | $-OC_2H_5$ | $-SC_3H_{7(n)}$ | $-C_2H_5$ | S |
| $-CH_3$ | $-OCH_3$ | $-SC_3H_{7(n)}$ | $-C_2H_5$ | S |

EXAMPLE 2

A. Insecticidal stomach poison action

Tobacco and potato plants were sprayed with a 0.05% aqueous active substance emulsion (obtained from a 10% emulsifiable concentrate).

After the drying of the coating, Egyptian cotton leaf worms (Spodoptera litoralis) were placed on the tobacco plants, and Colorada beetle larvae (Leptinotarsa decemlineata) on the potato plants. The test was carried out at 24° C. with 60% relative humidity.

The compounds according to Examples 1 and 2 exhibited in the above test stomach poison action against Spodoptera litoralis and Leptinotarsa decemlineata.

B. Systemic insecticidal action

In order to determine the systemic action, rooted bean plants (Vicia faba) were placed into a 0.01% aqueous active substance solution (obtained from a 10% emulsifiable concentrate). After a period of 24 hours, bean aphids (Aphis fabae) were placed on to the parts of the plants above the soil. The insects were protected by a special device from the effect of contact and of gas.

The test was carried out at 24° C with 70% relative humidity.

In the above tests, the compound according to Examples 1 and 2 exhibited stomach poison action and systemic insecticidal action.

EXAMPLE 3

Action against Chilo suppressalis

Rice plants of the type Caloro were planted, 6 plants per pot, in plastic pots have a top diameter of 17 cm, and grown to height of ca. 60 cm. Infestation with *Chilo suppressalis* larvae ($L_1$; 3-4 mm long) was carried out 2 days after application of the active substance in granule form (amount applied 8 kg of active substance per hectare) to the paddy water. The evaluation of the insecticidal action was made 10 days after application of the granules.

The compounds according to Examples 1 and 2 were effective against *Chilo suppressalis* in the above test.

EXAMPLE 4

Sterilised compost soil was homogeneously mixed with a wettable powder containing 25% of active substance, so that an applied amount of 8 kg of active substance per hectare resulted.

Young zucchetti plants (*Cucumis pepo*) were potted with the treated soil in plastic pots (three plants per pot of 7 cm diameter). The said pots were infested immediately afterwards with 5 *Aulacophora* femoralis larvae, 5 *Pachmoda* larvae and 5 *Chortophila* larvae, respectively: The assessment of the results were made 4, 8, 16 and 32 days after infestation with the larvae.

In the case of 80-100% destruction on the first assessment, a repeated infestation was carried out, 5 larvae being placed into the same sample of soil with 3 new zucchetti plants. Where the action was less than 80%, the remaining larvae were left in the test soil until the next control assessment. If a substance with an applied amount of 8 kg per hectare offered a 100% destruction, then subsequent tests were made with 4 and 2 kg of active substance per hectare, respectively.

The compounds according to Examples 1 and 2 were effective in the above test against *Aulacophora femoralis* larvae, *Pachmoda* larvae and *Chortophila* larvae.

EXAMPLE 5

Action against ticks

A. *Rhipicephalus bursa*

In each case, 5 adult ticks were placed into one small glass test tube and 50 tick larvae into another; the test tubes were then immersed for 1 to 2 minutes in 2 ml of an aqueous emulsion from a dilution series of 100, 10, 1 and 0.1 ppm of test substance. The tubes were then sealed with a standardised cotton plug, and inverted so that the active substance emulsion could be absorbed by the cotton wool.

An evaluation in the case of the adults was made after 2 weeks, and in the case of the larvae after 2 days. There were two repeats for each test.

The compounds according to Examples 1 and 2 were effective in the above test against adults, larvae and eggs of *Tetranychus urticae*.

B. (*Boophilus microplus* (larvae)

With a dilution series analogous to that in Test A, tests were carried out with 20 sensitive larvae and OP-resistant larvae, respectively (the resistance is with respect to diazinon compatibility).

The compounds according to Examples 1 and 2 were effective in these tests against adults and larvae of *Rhipicephalus* bursa and against sensitive and OP-resistant larvae, respectively, of *Boophilus microplus*.

EXAMPLE 6

Acaricidal action

*Phaseolus vulgaris* (bush beans) were infested, 12 hours before the test for acaracidal action, with an infested piece of leaf from a mass culture of *Tetranychus urticae*. The transferred mobile stages were sprayed with the emulsified test preparations from a chromatography-sprayer in a manner ensuring no running off of the spray liquor. An assessment was made after 2 to 7 days, by examination under a binocular, of the living and of the dead larvae, adults and eggs, and the results expressed in percentages. The treated plants were kept during the "holding time" in greenhouse compartments at 25° C.

The compounds according to Examples 1 and 2 were effective in the above test against adults, larvae and eggs of *Tetranychus urticae*.

EXAMPLE 7

Action against soil nematodes

In order to test the action against soil nematodes the active substances were added, in the concentration stated in each case, to soil infested with root-gall-nematodes (*Meloidogyne arenaria*), and the whole intimately mixed. In the one test series, tomato seedlings were planted immediately afterwards in the thus prepared soil, and in the other test series tomatoes were planted after a waiting time of 8 days.

For an assessment of the nematicidal action, the galls present on the roots were counted 28 days after the planting and sowing, respectively.

The active substances according to Examples 1 and 2 exhibited in this test a good action against *Meloidogyne arenaria*.

We claim:

1. A compound of the formula $$\begin{array}{c} R_1-N-\!\!\!-\!\!\!-N \\ \phantom{R_1-N}\diagdown\phantom{N}\diagup\phantom{N}\diagdown\phantom{O-P}\overset{X}{\underset{\parallel}{\phantom{P}}}\diagup R_3 \\ R_2-\!\!\!-\!\!\!\diagup N \diagdown\!\!\!-O-P \\ \phantom{R_2-N} \diagdown OR_4 \end{array}$$

wherein $R_1$ represents $C_1$-$C_5$-alkyl, cyclopentyl, cyclohexyl or unsubstituted phenyl, $R_2$ represents $C_1$-$C_5$-alkoxy or phenoxy, $R_3$ represents $C_1$-$C_5$-alkyl, $C_1$-$C_5$-alkoxy or $C_1$-$C_5$-alkylthio, $R_4$ represents $C_1$-$C_5$-alkyl and X represents oxygen or sulfur.

2. The compound according to claim 1 of the formula $$\begin{array}{c} CH_3 \diagdown \\ \phantom{CH_3}CH-N-\!\!\!-\!\!\!-N \\ CH_3 \diagup \phantom{CH-N}\diagdown\phantom{N}\diagup\phantom{N}\diagdown\phantom{O-P}\overset{S}{\underset{\parallel}{\phantom{P}}} \\ \phantom{CH_3}CH_3O-\!\!\!\diagup N\diagdown\!\!\!-O-P(OC_2H_5)_2 \end{array}$$

3. The compound according to claim 1 of the formula

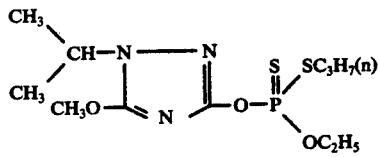

4. The compound according to claim 1 of the formula

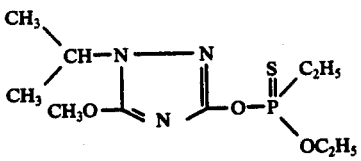

5. An insecticidal and acraicidal composition which contains as active component an insecticidally and acaricidally effective amount of a compound according to claim 1, together with a suitable inert carrier therefor.

6. A method of combatting insects and acarids which comprises applying to said insects and acarids or the locus thereof an insecticidally and acaricidally effective amount of a compound according to claim 1.

* * * * *